United States Patent [19]
Castagnaro et al.

[11] Patent Number: 5,592,951
[45] Date of Patent: Jan. 14, 1997

[54] ORAL APPLIANCE

[76] Inventors: Vincent Castagnaro, 533 Hawkins Rd., Selden, N.Y. 11784; Gerald J. Schnal, 191 Connetquot Ave., East Islip, N.Y. 11730-1416

[21] Appl. No.: 527,277

[22] Filed: Sep. 12, 1995

[51] Int. Cl.$^6$ ............................ A61F 5/56; A61C 5/14
[52] U.S. Cl. ................... 128/848; 128/859; 128/862
[58] Field of Search .................. 128/848, 846, 128/857, 858, 859, 860, 861, 862

[56] References Cited

U.S. PATENT DOCUMENTS

| | | | |
|---|---|---|---|
| 4,304,227 | 12/1981 | Samelson | 128/848 |
| 4,718,662 | 1/1988 | North | 128/860 |
| 4,955,393 | 9/1990 | Adell | 128/859 |
| 5,462,066 | 10/1995 | Snyder | 128/861 |
| 5,467,783 | 11/1995 | Meade | 128/859 |

Primary Examiner—Michael A. Brown
Attorney, Agent, or Firm—Galgano & Burke

[57] ABSTRACT

An oral appliance comprising an upper channel, adapted to receive upper teeth or gums, a roof wall comprising an upper surface adapted to generally conform to the roof of a user's mouth and a lower surface for engagement with a user's tongue; means for maintaining a lower jaw in a forward position, and at least one interior air passage.

18 Claims, 2 Drawing Sheets

ORAL APPLIANCE

The present invention is directed to oral appliances and, more particularly, to oral appliances designed to minimize the occurrence of sleep disorders such as sleep apnea and snoring.

BACKGROUND OF THE INVENTION

It is generally accepted that snoring and obstructive sleep apnea (OSA) are due to complete or partial collapsing of the air passageway in the back of the throat (the pharynx). Soft tissue, such as the tongue along with other soft tissue including the soft pallet and uvula, can obstruct nasal breathing during sleeping. Previously disclosed dental devices have been designed to alleviate the disruptive effects of snoring and sleep apnea. Many of such devices have been designed to either advance the lower jaw in a forward position or to hold the tongue forwardly in the mouth in order to keep the pharynx open.

One such device known as the nasal continuous positive airway pressure (CPAP) mask supplies super atmospheric pressure air from a pump to the nose and throat area to create a pressure differential against atmospheric pressure air in the mouth to keep the airway open. The CPAP employs a pump and facial mask which must be worn by a user. While the CPAP has been reported and proven effective in approximately 85 percent of all OSA sufferers, the CPAP has disadvantages. For example, some users cannot tolerate wearing the mask during sleep, some users complain of dry mouth and nose, sore throat, eye irritations and ear infections. Furthermore the noise of the pump and mask can be disturbing to a bedroom partner. Still furthermore, the nasal CPAP is cumbersome and not easily transported when a user travels.

It would therefore be desirable to provide an oral appliance which is readily transportable and which is capable of providing relief to people suffering from sleep disorders such as apnea and snoring.

It would also be desirable to provide the pressure differential advantages of a nasal CPAP apparatus in a small portable dental appliance.

SUMMARY OF THE INVENTION

One aspect of the present invention comprises an oral appliance comprising an upper channel adapted to receive upper teeth or gums, a substantially arcuate upper sidewall and a base, a roof wall connected to the lower wall wherein the roof wall comprises an upper surface adapted to generally conform to the roof of a user's mouth and a lower surface for engagement with a user's tongue, means for maintaining a lower jaw in a forward position, and at least one air passage extending through the base.

One embodiment of the present invention comprises a passageway which extends through a tooth/gum base of the oral appliance and advantageously facilitates a pressure differential between air in the pharynx and air in the mouth in order to maintain the pharynx in an open position during sleeping. According to one preferred embodiment, an air passageway extends from an upper channel to a lower channel. In another preferred embodiment, an air passageway extends from an upper channel through a roof wall and terminates through a lower surface of a roof wall.

According to another preferred embodiment of the present invention, an oral appliance comprises first portions having a first thickness and at least one other portion having a greater thickness.

Preferred embodiments of the present invention can be formed of relatively inexpensive thermoplastic materials and can be easily customized to comfortably fit within the mouth of a user. These and other advantages are described below with reference to the drawings.

DETAILED DESCRIPTION

The various embodiments of the present invention are directed to oral appliances specifically designed to minimize the occurrence of sleep disorders such as sleep apnea and snoring. The various embodiments of the present invention advantageously comprise relatively inexpensive, easily manufactured oral appliances which may be readily customized to fit a user's mouth. Furthermore, the various embodiments of the present invention advantageously comprise at least one air passageway which facilitates an air pressure differential between the forward portion of the mouth and the pharynx. The novel air passageways of the embodiments of the present invention advantageously draw the tongue forward while urging the soft pallet into a forward position in order to maintain the pharynx in an open position.

Figure 1:
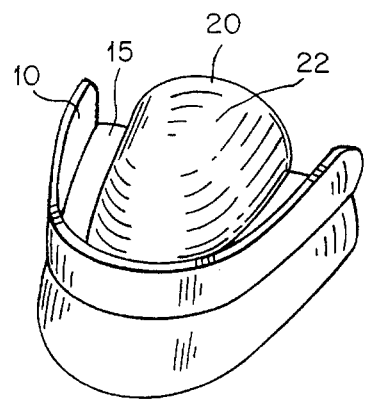
FIG. 1 is a perspective view of an oral appliance of one embodiment of the present invention.
Figure 2A:
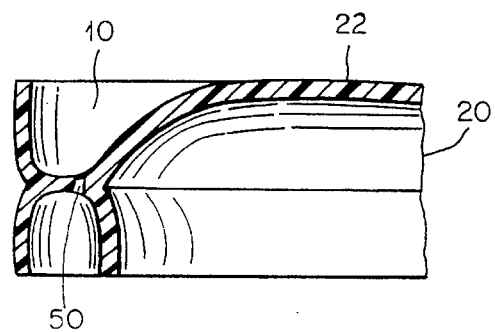
FIG. 2A is a cross-sectional view taken along lines 2A—2A of FIG. 2.
Figure 2:
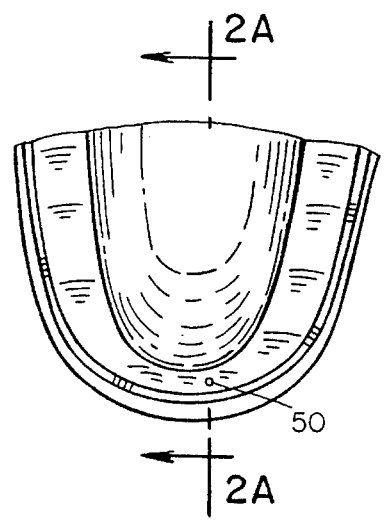
FIG. 2 is a top view of the oral appliance shown in FIG. 1.
Figure 3:
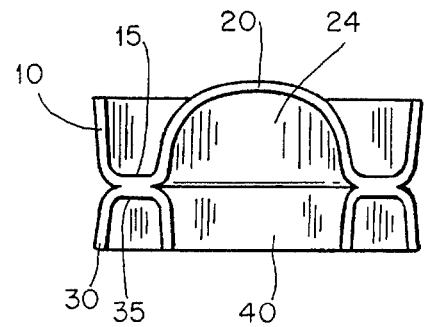
FIG. 3 is a rear view of the oral appliance shown in FIG. 1.

One embodiment of the present invention illustrated in FIGS. 1 to 3 comprises an upper channel defined by a substantially arcuate upper side wall 10, a base 15 and a roof 20 comprising an upper surface 22 and a lower surface 24. This illustrated embodiment also comprises a lower channel defined by lower outer wall 30, lower base 35 and lower inner wall 40. The interior surface 24 of roof 20 and the interior surface of lower, inner wall 40 are preferably substantially smooth for comfortable engagement with the user's tongue. This configuration is designed to maintain a person's mouth in a closed position during sleeping and to prevent the lower jaw from sliding too far rearwardly toward the user's throat during sleeping. The preferred illustrated embodiments advantageously maintain the mandibular forward of its normal at rest position. The soft pallet and the tongue are also preferably maintained in a forward position in order to maintain an open passageway for unobstructed breathing.

This illustrated embodiment is generally formed of an upper portion and a lower portion which have been joined by heat sealing. Those skilled in the art will appreciate that the various embodiments of the present invention are readily formed in a single mold and can be formed as a unitary device of thermoplastic material in different sizes. In this manner, a user may customize the fit of the oral appliance by first softening the appliance with heat, for example, by immersing in hot water, then fitting the appliance within the user's mouth and, subsequently, upon cooling, the appliance will retain the customized form unless subjected to elevated temperatures.

Various materials may be utilized in forming the oral appliances of the present invention. Suitable materials include thermoplastics such as ELVAX™ made by DuPont of Wilmington, Del., U.S.A., various plastics or plastic resins, polycarbonates or other castable materials such as acrylics, polyprophylene, or various combinations thereof. Furthermore, the thickness of the material can vary without departing from the scope of the present invention. For example, suitable thicknesses include about 0.02 to about 0.15 inches.

One advantageous feature of the various embodiments of the present invention is the provision of at least one air passage. The air passage is preferably provided through the base or bases in order to connect the upper channel and lower channel. It has been determined that the provision of such an air passage advantageously facilitates the creation of a pressure differential between the forward interior portion of the mouth and the pharynx. Those skilled in the art will appreciate that the number and positioning of such air passageways can affect the magnitude of a pressure differential.

FIG. 2A illustrates the direction and extent of air passage 50 in the embodiment illustrated in FIGS. 1–3.

Figure 4:
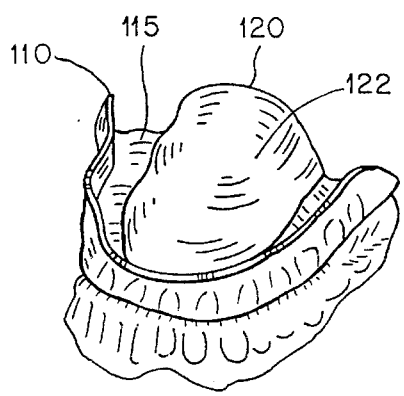
FIG. 4 is a perspective view of an oral appliance of an alternative embodiment of the present invention after thermal fitting.
Figure 5:
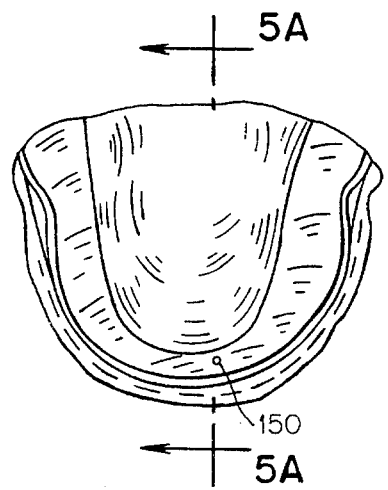
FIG. 5 is a top view of the oral appliance shown in FIG. 4.
Figure 5A:
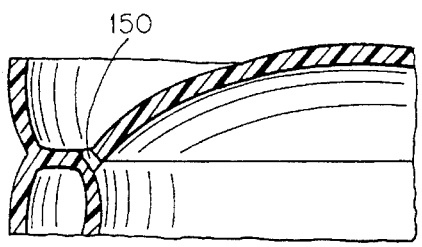
FIG. 5A is a cross-sectional view taken along lines 5A—5A of FIG. 5.
Figure 6:
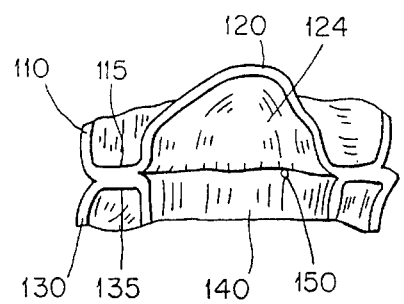
FIG. 6 is a rear view of the oral appliance shown in FIG. 4.

According to another embodiment of the present invention illustrated in FIGS. 4–6, an air passage 150 extends from the upper surface of base 115 on an angle to the inner surface 124 of roof wall 120. From the illustrations and the present description, those skilled in the art will appreciate that the embodiment illustrated in FIGS. 4–6 has been fitted to a user whereas the embodiment illustrated in FIGS. 1–3 is a blank which may either be worn as illustrated or can be customized in a manner known in the art. The position of air passage 150, as best shown in FIG. 5A, maximizes the forward suction on the tongue against the interior surface of roof wall 124. In order to minimize any discomfort to the user's tongue, the terminal portions of the air passages are preferably smooth and/or beveled in order to avoid any sharp edges. Those skilled in the art will appreciate that all surfaces of the oral appliances of the present invention are preferably sufficiently and/or resilient to avoid unnecessary discomfort to the user.

Figure 7:
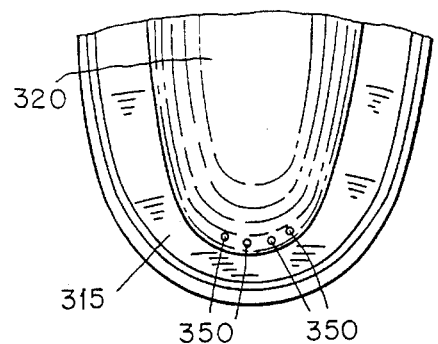
FIG. 7 is a top view of a still further embodiment of the present invention.

While the embodiment of the present invention illustrated in FIGS. 1 to 3 is provided with a single air passage 50, it is also within the scope of the present invention to provide a plurality of such air passages. A still further embodiment of the present invention is illustrated in FIG. 7 wherein an oral appliance comprises a plurality of air passages 350 extending entirely through roof wall 320. As shown in this embodiment, the air passages are advantageously disposed proximate to the base 315.

Figure 8:
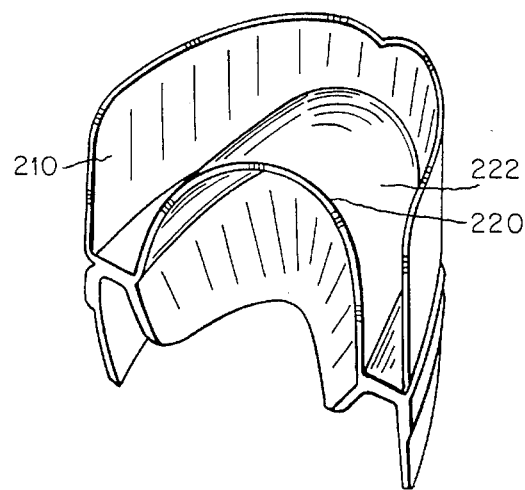
FIG. 8 is a rear perspective view of a still further embodiment of the present invention.
Figure 9:
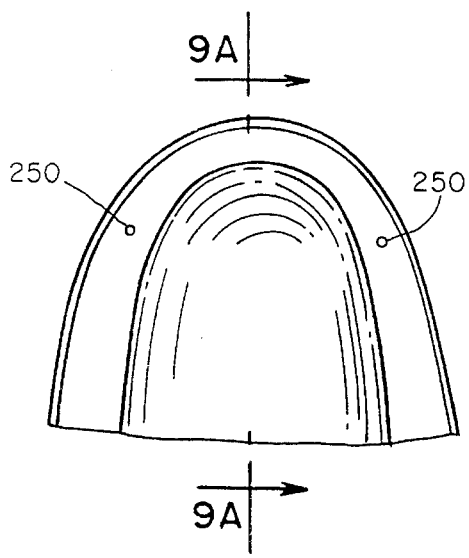
FIG. 9 is a top view of the embodiment illustrated in FIG. 8.
Figure 9A:
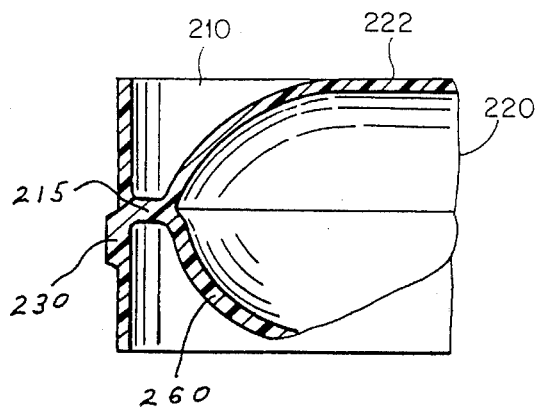
FIG. 9A is a cross-sectional view taken along lines 9A—9A of FIG. 9.

Another preferred embodiment of the present invention is advantageously designed to eliminate the need for thermal fitting. According to this preferred embodiment which is illustrated in FIGS. 8–9A, an upper sidewall 210 and a roof wall 222 are advantageously formed relatively thin so as to provide resilience during use. For example, these portions may be formed of one or more of the thermoplastic material stated above and having a thickness of about 0.02 inches so that they are flexible when in use. At least one other portion of this illustrated embodiment comprises a thicker portion. As best shown in FIG. 9A, according to this illustrated embodiment, base 215 and at least a portion of lower outer wall 230 are formed having a greater thickness, for example about 0.04 inches. According to another advantageous aspect of this illustrated embodiment, the lower inner wall 260 extends-rearwardly on a downwardly sloping angle for a significant portion of the entire depth of the appliance. For example, the rearward component of the extension of this lower inner wall 260 preferably comprises at least 20 percent and most preferably at least 30 percent of the entire length of the device. As used herein, the length is used to indicate the forward to rearward extent of the device as the device is positioned within a mouth. As illustrated, this inner, lower wall 260 is preferably also formed with a thickness greater than roof wall 222. This embodiment is designed to advantageously surround the user's tongue to a greater degree. While this illustrated embodiment comprises two air passageways 250 extending through base 215, it is also within the scope of the present invention to provide an oral appliance having different portions with different thicknesses and with one or more air passageways as set forth herein. The embodiment of the present invention illustrated in FIGS. 8–9A comprises portions which are advantageously sufficiently resilient to readily conform to the contours of a user's mouth during use while having other sufficiently rigid portions for maintaining the appliance in position.

It is believed that swallowing by a user tends to create a suction in the upper channels of the various embodiments of the present invention which thereby tend to create a lower pressure in the interior of the mouth as compared to the pharynx. The various embodiments help to alleviate the adverse effects of snoring and sleep apnea by maintaining the mandibular and tongue forward. Furthermore, the pressure differential keeps the soft palate forward. The various embodiments of the present invention advantageously significantly reduce the adverse effects of snoring and sleep apnea.

What is claimed is:

1. An oral appliance comprising:

an upper channel, adapted to receive upper teeth or gums, comprising a substantially arcuate upper sidewall and a base;

a roof wall connected to said upper channel, said roof wall comprising an upper surface adapted to generally conform to the roof of a user's mouth and a lower surface for engagement with a user's tongue;

means for maintaining a lower jaw in a forward position, said mantaining means extending downwardly from said upper channel; and at least one air passage extending through said base.

2. An oral appliance according to claim 1 wherein said maintaining means comprises at least one substantially arcuate, inner sidewall.

3. An oral appliance according to claim 2 further comprising a lower, outer sidewall.

4. An oral appliance according to claim 3 wherein said air passage defines an orifice disposed between a lower inner sidewall and said lower outer sidewall.

5. An oral appliance according to claim 1 wherein said at least one air passage extends downwardly passing entirely through said base.

6. An oral appliance according to claim 5 wherein said air passage has a diameter of about 0.1–0.2 cm.

7. An oral appliance according to claim 5 comprising a plurality of air passages.

8. An oral appliance according to claim 1 wherein said at least one air passage extends on an angle from an upper surface of said base to an interior surface defined by said lower surface of said roof wall and said maintaining means.

9. An oral appliance according to claim 1 wherein said at least one passage extends from an upper surface of said base to said lower surface of said roof wall.

10. An oral appliance according to claim 9 wherein said at least one air passage has a diameter of about 0.1–0.2 cm.

11. An oral appliance according to claim 9 comprising a plurality of air passages.

12. An oral appliance according to claim 1 wherein said oral appliance is integrally formed of a thermoplastic material.

13. An oral appliance according to claim 1 wherein said maintaining means also extends rearwardly.

14. An oral appliance according to claim 13 wherein said maintaining means extends rearwardly for a distance of at least 20 percent of the length of said oral appliance.

15. An oral appliance according to claim 13 wherein said maintaining means extends rearwardly for a distance of at least 30 percent of the length of said oral appliance.

16. An oral appliance according to claim 1 wherein at least a first portion is formed having a first thickness and at least a second portion is formed having a second thickness which is greater than said first thickness.

17. An oral appliance according to claim 16 wherein said roof wall is formed having said first thickness and at least a portion of said maintaining means is formed having said second thickness.

18. An oral appliance according to claim 17 wherein said oral appliance further comprises at outer lower wall at least a portion of which is formed having a thickness greater than said first thickness.

* * * * *